United States Patent [19]
Graebner et al.

[11] Patent Number: 5,625,449
[45] Date of Patent: Apr. 29, 1997

[54] APPARATUS FOR SIMULTANEOUSLY MEASURING THE THICKNESS OF, AND THE OPTICAL INTENSITY TRANSMITTED THROUGH, A SAMPLE BODY

[75] Inventors: John E. Graebner, Short Hills; Sungho Jin, Millington, both of N.J.

[73] Assignee: Lucent Technologies Inc., Murray Hill, N.J.

[21] Appl. No.: 509,410

[22] Filed: Jul. 31, 1995

[51] Int. Cl.⁶ .................................................. G01N 21/59
[52] U.S. Cl. ........................................ 356/72; 356/440
[58] Field of Search ............................. 356/72, 73, 440

[56] References Cited

U.S. PATENT DOCUMENTS 3,414,725  12/1968  Evans .................................. 356/72 X
4,023,909   5/1977  Ross ................................. 356/440 X
5,028,787   7/1991  Rosenthal et al. ................. 250/343 X

FOREIGN PATENT DOCUMENTS 63-273043  11/1988  Japan ................................... 356/440

*Primary Examiner*—Vincent P. McGraw
*Attorney, Agent, or Firm*—David I. Caplan

[57] ABSTRACT

A portion of a surface of a sample body is arranged to receive an incident optical beam having an optical intensity $I_0$. On an opposing surface of the sample body is located an optical detector which senses the intensity I of the resulting optical radiation emerging from the opposing surface of the sample body. In order to measure the thickness t of the sample body, a thickness gauge is located either at another portion of the surface of the sample body or on the optical detector.

2 Claims, 1 Drawing Sheet

APPARATUS FOR SIMULTANEOUSLY MEASURING THE THICKNESS OF, AND THE OPTICAL INTENSITY TRANSMITTED THROUGH, A SAMPLE BODY

FIELD OF THE INVENTION

This invention relates to apparatus for measuring the thickness of, and the optical intensity transmitted through, a sample body—and more particularly for measuring both the optical intensity emerging from a major surface of the sample body, in response to optical radiation incident on an opposing major surface of the sample body, and the thickness of the sample body, preferably simultaneously.

BACKGROUND OF THE INVENTION

Our patent applications Graebner-Jin 10-109 and Graebner-Jin 11-110, filed simultaneously herewith and hereby incorporated herein, teach methods and apparatus for determining the thermal conductivity of electrically insulating crystalline materials. These methods and apparatus require determinations of the thickness and optical absorptivity of a sample body. To these ends it would be desirable to have apparatus for measuring both the optical intensity I emerging from a major surface of the sample body, in response to optical radiation of intensity $I_0$ incident on an opposing major surface of the sample body, and the thickness t of the sample body. Advantageously, the apparatus should be capable of determining both the emerging optical intensity I and the thickness t simultaneously.

SUMMARY OF THE INVENTION

This invention provides apparatus capable of simultaneously detecting both the optical intensity I emerging from a major surface of the sample body, in response to optical radiation of intensity $I_0$ incident on an opposing major surface of the sample body, and the thickness t of the sample body. Preferably the apparatus is arranged so as to be capable of determining both the emerging optical intensity I and the thickess t simultaneously.

In a specific embodiment of the invention, a portion of a major surface of the sample body is arranged to receive an incident optical beam having an optical intensity $I_0$. On a portion of an opposing major surface of the sample body is located an optical detector which senses the intensity I of the optical radiation emerging from the opposing major surface of the sample body in response to the incident optical beam. The output of the detector is a representative of the value of the optical intensity I of the the resulting optical intensity emerging from an opposing major surface of the body. A thickness measuring device ("thickness gauge") is located either at another portion of the major surface of the sample body or on the optical detector. The output of the thickness gauge is a representative of the desired value of the thickness t of the sample body.

DETAILED DESCRIPTION

Figure 1:
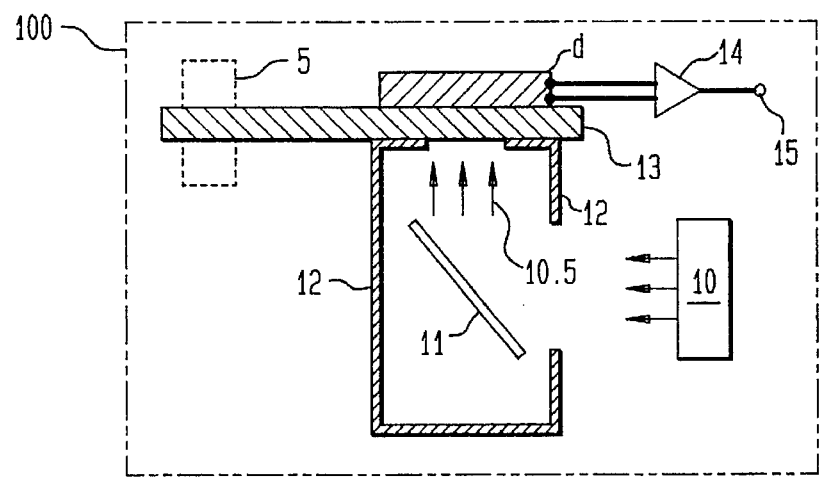
FIG. 1 is a diagram, partly in cross section, of apparatus capable of simultaneously measuring both the optical intensity I emerging from a major surface of a sample body, in response to optical radiation of intensity $I_0$ incident on an opposing major surface of the sample body, and the thickness t of the sample body, in accordance with a specific embodiment of the invention.

FIG. 1 shows apparatus 100 for measuring simultaneously the thickness t of a sample body 13 and the optical intensity I of optical radiation emerging from the sample body 13. As shown in FIG. 1, an optical source 10 is arranged to produce an optical beam incident on a mirror 11 located in a chamber 12. The chamber 12 has an aperture on its side wall to enable the beam to be incident on the mirror 11. The chamber 12 has inside walls that are non-reflecting, such as metallic walls painted with black paint or metallic walls comprising anodized aluminum. As a result, a reflected optical beam 10.5 having an intensity $I_0$ emerges from the mirror 11.

As further shown in FIG. 1, on the top wall of the chamber 12 another aperture is located. A sample body 13 is located on this aperture, whereby the optical beam 10.5 illuminates a bottom major surface of the sample body 13. An optical detector d is located on a top major surface of the sample body 13, whereby this detector d senses the optical intensity I emerging from the top surface of the sample body 13. The detector d thus develops an output that is representative of this optical intensity I. Amplifier circuitry 14 is arranged to receive the output of the detector d and produces an amplifier circuitry output at terminal 15.

The intensity $I_0$ of the optical beam 10.5 can be measured simply by removing the sample 13 and allowing the beam 10.5 to impinge directly on the detector d, without having gone through the sample body 13. Simultaneously, the thickness of the sample 13 can be measured by the thickness gauge 5.

As further indicated in FIG. 1, at the same time that the value of I or $I_0$ is thus being measured, the value of the thickness t of the sample body 13 can be measured by means of a thickness measuring device ("a thickness gauge") 5. This thickness gauge 5 can take many forms, such as a simple caliper, a Vernier caliper, or an optical thickness gauge such as a HEIDENHAIN-METRO MT 12/MT 25 or MT 12B/MT 25 Digital Length Gauge supplied by Dr. JOHANNES HEIDENHAIN GmbH, Strasse 5, D-8225. Traunreut, Germany.

Here in FIG. 1, it is assumed that the thickness t of the sample body 13 is substantially the same in the region of the thickness gauge 5 as it is in the region of the aperture located at the top of the chamber 12.

Figure 2:
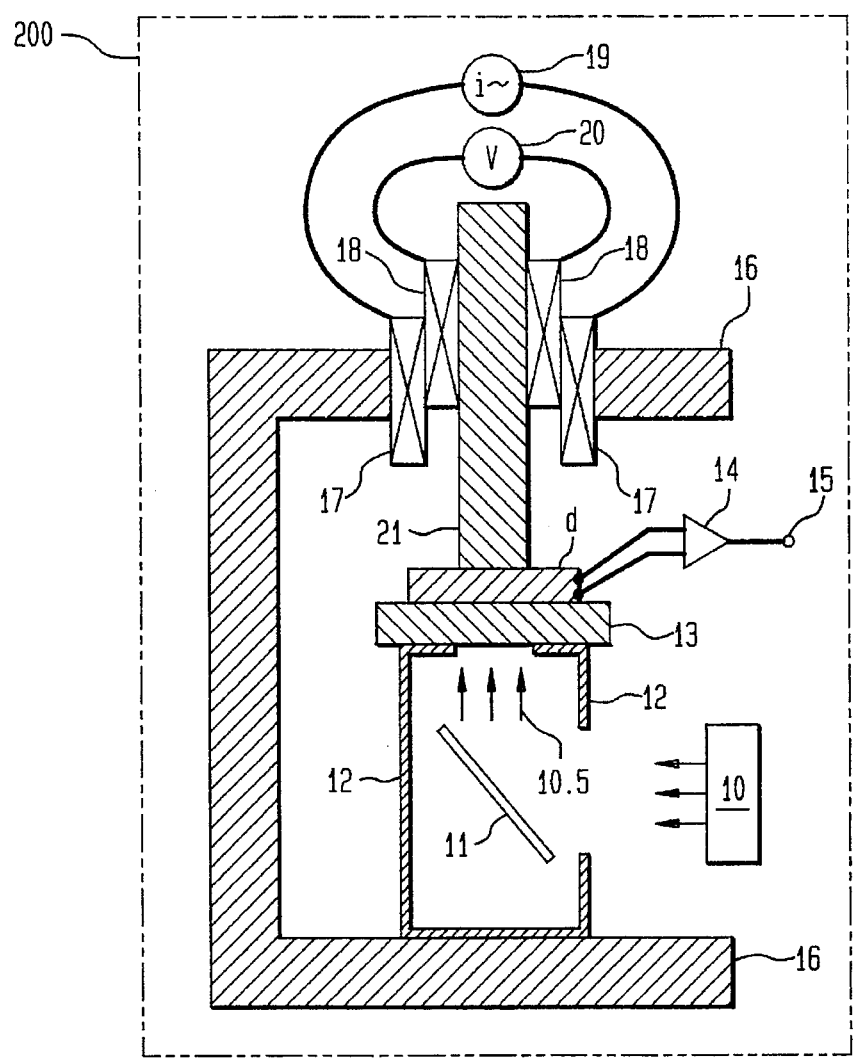
FIG. 2 is a diagram, partly in cross section, of apparatus capable of simultaneously measuring both the optical intensity I emerging from a major surface of a sample body, in response to optical radiation of intensity $I_0$ incident on an opposing major surface of the sample body, and the thickness t of the sample body, in accordance with another specific embodiment of the invention.

FIG. 2 shows another apparatus 200 for measuring simultaneously the thickness t of the sample body 13 in a region and the optical intensity I of optical radiation emerging from the sample body 13 in the same region. Elements that are similar or identical to those shown in FIG. 1 are denoted by the same reference numerals or labels. As indicated in FIG. 2, the bottom of the chamber 12 is fixed to a U-shaped frame 16, typically made of metal that is nonmagnetic. The top rung of the frame 16 has an aperture. A primary coil 17 is fixed to this aperture. A secondary coil 18 is free to slide along the primary coil 17. The primary coil 17 is driven by an a.c. current source 19 typically having a frequency in the approximate range of 100 Hz to 100 kHz. A plunger 21 made of non-magnetic material such as linen-based Bakelite is fixed to the secondary coil 17. Also, a bottom surface of the plunger 21 is fixed to the top surface of the optical detector d.

An a.c. voltmeter 20 is connected across the secondary coil 18, whereby the voltmeter 20 senses a voltage that is proportional to the mutual inductance M between the coils 17 and 18. Since this mutual inductance M is proportional to the distance between the bottom of the primary coil 17 and the bottom of the secondary coil 18, changes in readings of the voltmeter 20 are proportional to increments in the distance that the plunger 21 has moved in the vertical direction. Thus the difference in the voltages sensed by the voltmeter 20 when the sample body 13 is in place as opposed to when the sample body 13 is removed (and hence when the bottom surface of the detector d sits on the top surface of the chamber 12) is a representative of the thickness t of the sample body 13. The optical intensities I and $I_0$ can be measured in the apparatus 200 in the same way as described above for measuring these intensities in the apparatus 100.

The primary coil 17, the secondary coil 18, the a.c. current source 19, and the plunger 21 form a linear differential displacement transformer, as known in the art.

Although the invention has been described in detail with respect to specific embodiments, various modifications can be made without departing from the scope of the invention. For example, the optical source 10 can be located within the chamber 12, and at the same time the optical beam emitted by this optical source 12 can be directed at the bottom surface of the sample body 13, whereby the mirror 11 can be omitted. Also, instead of determining the thickness t of the sample 13 by measuring mutual inductance (FIG. 2), self inductance of the primary coil 17 can be measured by omitting the secondary coil 18 and constructing the plunger 21 in such a manner that it comprises a soft magnetic portion and a nonmagnetic portion, the boundary between the two portions being located within the region of the primary coil 17. The differential displacement transformer need not be linear so long as its calibration of voltage vs. position is first measured.

What is claimed is:

1. Apparatus for measuring the thickness t and the intensity I of light emerging from a first major surface of a sample solid body, having first and second opposing major planar surfaces, comprising:

(a) a source of optical radiation for directing a beam of optical radiation on a first portion of said second major surface of the sample body, said source of radiation comprising a light source, a mirror and a hollow chamber enclosing said mirror, said chamber having a planar exterior surface for supporting said second major surface of said sample body, a first aperture for permitting a light beam from said light source to shine on said mirror and a second aperture in said planar exterior surface for permitting exit of a beam reflected by said mirror onto said sample body;

(b) an optical detector located on a second portion of the first major surface of the sample body, the second portion being the first major surface being located opposed to the first portion of the second major surface; and (c) a thickness measuring device comprising a differential displacement transformer located on the optical detector.

2. Apparatus according to claim 1 in which the thickness measuring device is a linear differential displacement transformer.

\* \* \* \* \*